US00PP36787P2

(12) United States Plant Patent
Grazzini

(10) Patent No.: US PP36,787 P2
(45) Date of Patent: Jul. 1, 2025

(54) ***SYRINGA* PLANT NAMED 'G13110'**

(50) Latin Name: *Syringa hybrida*
Varietal Denomination: G13110

(71) Applicant: GardenGenetics LLC, Columbus, OH (US)

(72) Inventor: Richard A. Grazzini, Bellefonte, PA (US)

(73) Assignee: GardenGenetics LLC, Columbus, OH (US)

( * ) Notice: Subject to any disclaimer, the term of this patent is extended or adjusted under 35 U.S.C. 154(b) by 0 days.

(21) Appl. No.: 19/004,681

(22) Filed: Dec. 30, 2024

(51) Int. Cl.
*A01H 5/00* (2018.01)
*A01H 6/00* (2018.01)

(52) U.S. Cl.
USPC ..... Plt./248

(58) Field of Classification Search
USPC ..... Plt./226, 248
See application file for complete search history.

(56) References Cited

U.S. PATENT DOCUMENTS

PP30,286 P2 * 3/2019 Selinger ..... A01H 5/02 Plt./248

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct cultivar of *Syringa* plant, referred to by its cultivar name, 'G13110', is described. The new variety forms light pink-colored flowers which are strongly fragrant. Dark-green-colored foliage is formed, and the new variety is moderately vigorous and densely branched. The growth habit is compact. The new variety is particularly well suited for growing as distinctive ornamentation in the landscape.

2 Drawing Sheets

Figure 1:
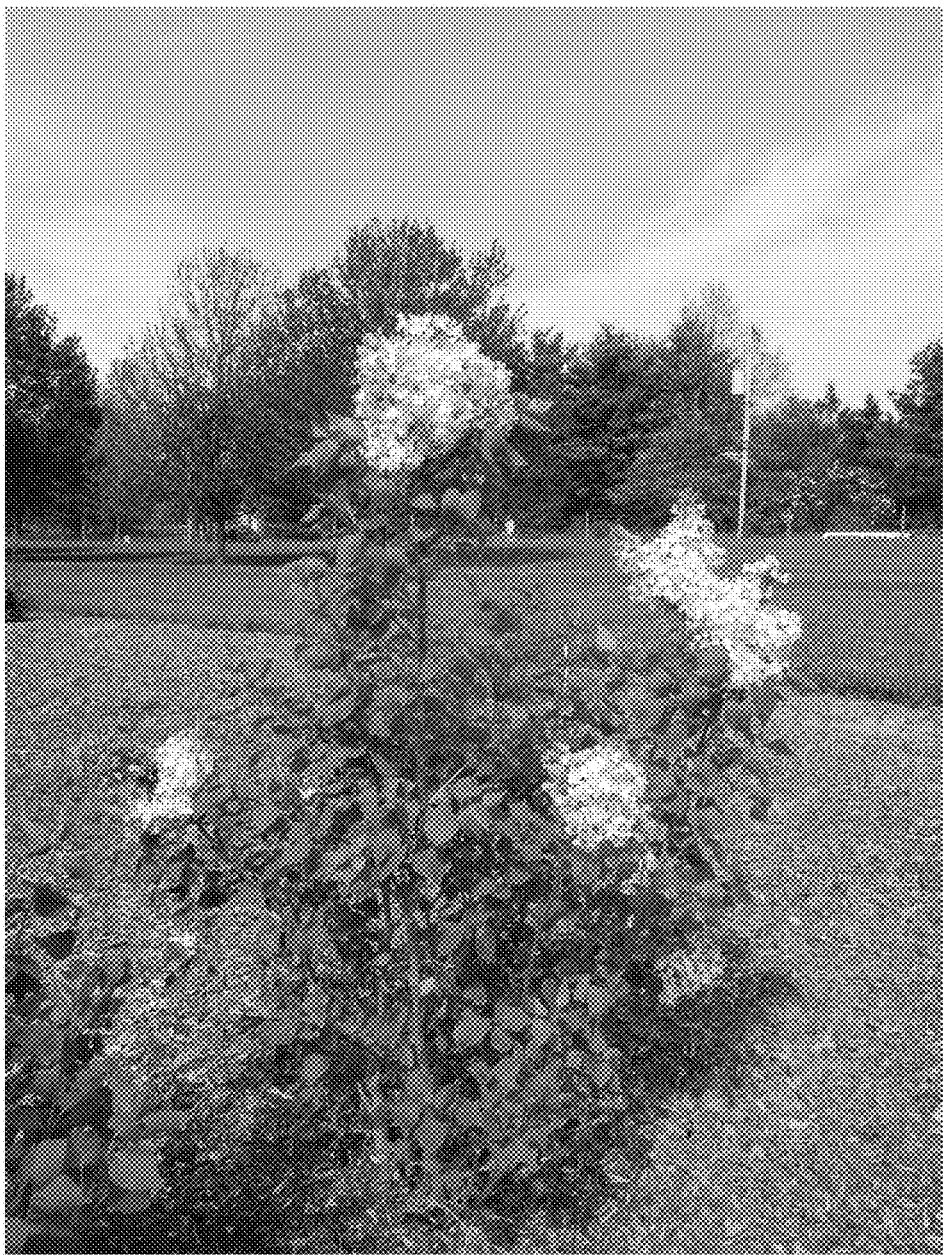

Latin name of genus and species of plant claimed: *Syringa hybrida.*

Variety denomination: 'G13110'.

STATEMENT REGARDING PRIOR DISCLOSURES BY THE INVENTOR

The first offer for sale of the new variety was July 2024, in Columbus, Ohio at the Cultivate Trade Show. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The present invention relates to a new and distinct cultivar of *Syringa* plant botanically known as *Syringa hybrida* and hereinafter referred to by the cultivar name 'G13110'.

The new cultivar originated in a controlled breeding program in Bellefonte, Pennsylvania during May 2009. The objective of the breeding program was the development of a series of *Syringa* cultivars with a faster production cycle, compact habits, and strong powdery mildew resistance.

The new cultivar was created by cross-pollination wherein two parents were crossed which previously had been studied in the hope that they would contribute the desired characteristics. The female parent (i.e., the seed parent) of the new cultivar is *Syringa* x *hyacinthiflora*

'Maidens Blush' (not patented). The male parent (i.e., the pollen parent) of the new cultivar is a non-patented unnamed breeder seedling.

The parentage of the new variety can be summarized as follows:

'Maidens Blush' x unnamed breeder seedling

The new cultivar was discovered and selected as a single flowering plant within the progeny of the above stated cross-pollination during May 2013 in a controlled environment in Bellefonte, Pennsylvania.

SUMMARY OF THE INVENTION

It was found that the new variety of *Syringa* plant of the present invention possesses the following combination of characteristics:

(a) forms light pink colored, strongly fragrant flowers,
(b) exhibits dark green-colored foliage, and
(c) displays a densely branched and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Maidens Blush' variety (i.e., the seed parent) displays bicolor, pink-colored flowers, provides medium green-colored foliage, and exhibits a moderately vigorous compact growth habit, whereas the new variety displays lighter pink-colored flowers, provides darker green colored foliage, exhibits a more densely branching growth habit, and has an increased resistance to lilac powdery mildew compared to the seed parent. In addition, the unnamed breeder seedling male parent (i.e., the pollen parent) displays white colored flowers, provides medium green-colored foliage, and exhibits a moderately vigorous and somewhat sprawling growth habit, compared to the new variety that displays pink-colored flowers, provides a darker green colored foliage, and exhibits more upright and densely branching growth habit. Moreover, the new variety can be readily distinguished from related similar non-parental varieties. For example, the 'Katherine Havemeyer' variety (not patented) is the most similar commercially available cultivar and exhibits a less dense growth habit and decreased resistance to powdery mildew compared to the new variety.

The new variety has been found to undergo asexual propagation at Bellefonte, Pennsylvania by softwood cuttings. Asexual propagation by softwood cuttings at Bellefonte, Pennsylvania has shown that the characteristics of the new variety are stable and are strictly transmissible by such asexual propagation from one generation to another. Accordingly, the new variety undergoes asexual propagation in a true-to-type manner.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'G13110'. The *Syringa* plants of the new variety were grown in a field in Cochranville, Pennsylvania for approximately three years. Photographs were taken May 4, 2018.

FIG. 1—illustrates a side view of the overall growth and flowering habit of 'G13110'.

Figure 2:
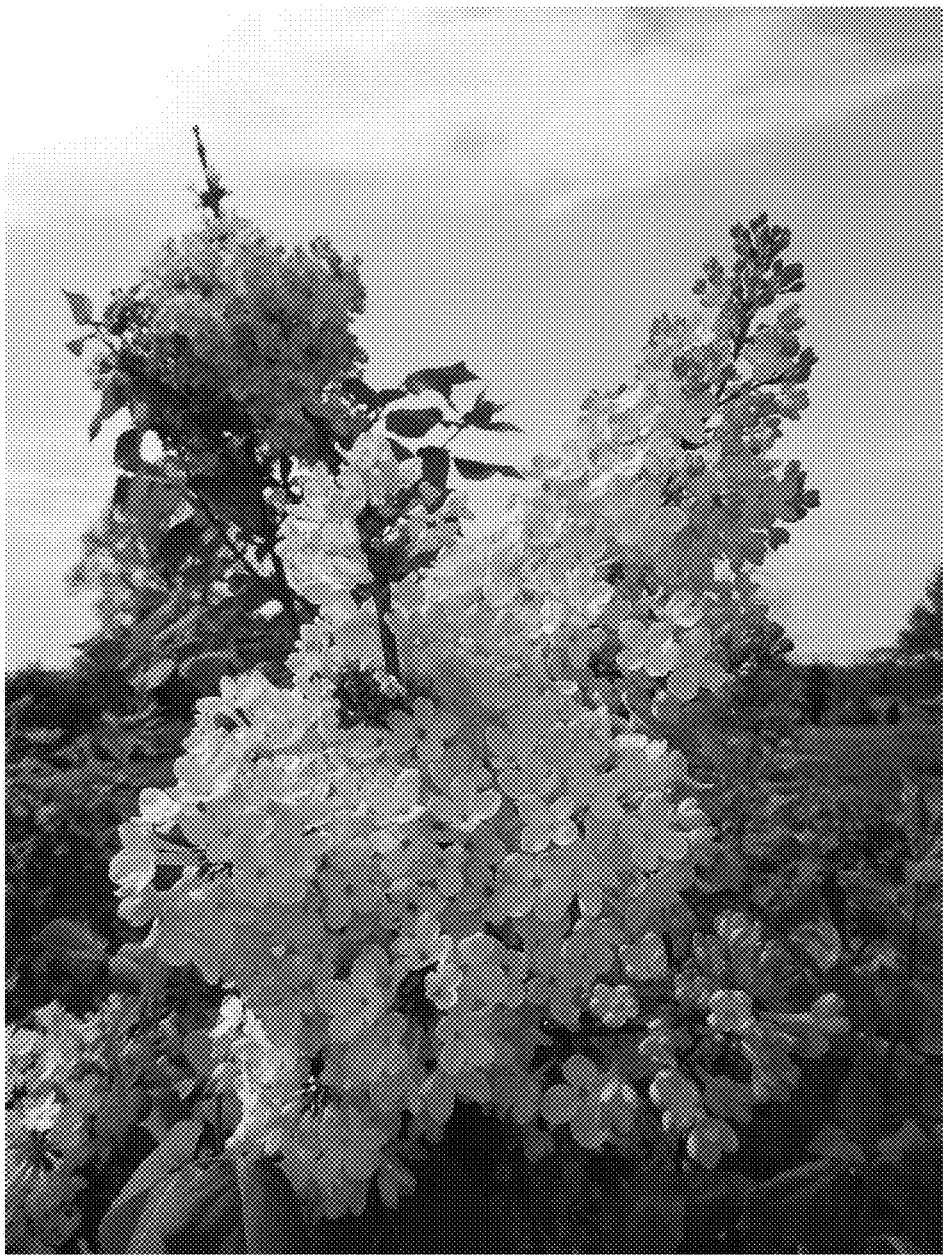

FIG. 2—illustrates a close-up view of an inflorescence of 'G13110'.

DETAILED BOTANICAL DESCRIPTION

The chart used in the identification of colors described herein is The R.H.S. Colour Chart of The Royal Horticultural Society, London, England, 2015 edition, except where general color terms of ordinary significance are used. The color values were determined in May 2020 under natural light conditions in Cochranville, Pennsylvania.

The following descriptions and measurements describe plants produced from cuttings from stock plants. The plants were grown outside in a field on their own roots for approximately five years. Measurements and numerical values represent averages of typical plants.

Botanical classification: *Syringa hybrida* cultivar 'G13110'.

Propagation:

*Type cutting*.—Softwood cuttings.

*Time to initiate roots*.—Approximately 5 weeks.

*Time to produce a rooted cutting*.—Approximately 11 weeks.

*Root description*.—Fibrous and fine; white to brown in color.

*Rooting habit*.—Freely branching; dense.

Plant:

*Habit*.—Densely branched and compact.

*Commercial crop time*.—Approximately 10-11 months from a 4-inch liner to finish in a three-gallon container.

*Growth habit and general appearance*.—Flowering shrub, densely branched and compact growth habit.

*Hardiness*.—USDA Zone 4.

*Size*.—Height: approximately 135.0 cm on average. — width: approximately 135.0 cm on average.

*Branching habit*.—Freely branching. — quantity of branches per plant: approximately 7 main stems per plant with approximately 5 to 7 lateral branches per stem on average.

*Lateral branches*.—Strength: strong. — length: approximately 30.0 cm on average. — diameter: approximately 1.0 cm on average. — length of central internode: approximately 3.0 cm on average. — texture of mature stem: woody. — color of mature stems: Grey-Brown Group N200B.

Foliage:

*General description*.—Form: simple. — arrangement: alternate. — fragrance: none detected.

*Leaves*.—Aspect: 45° to stem. — shape: deltoid. — margin: entire. — apex: acute. — base: truncate. — venation pattern: pinnate. — length of mature leaf: approximately 6.0 cm on average. — width of mature leaf: approximately 5.5 cm on average. — texture of upper and lower surfaces: glabrous. — color of upper surface of developing foliage: Green Group 138A with venation of Green Group 138B. — color of lower surface of developing foliage: Green Group 138B with indistinguishable venation. — color of upper surface of mature foliage: Green Group NN139A with venation of Yellow-Green Group 144A. — color of lower surface of mature foliage: Green Group 137C with venation of Yellow-Green Group 144A.

*Petiole*.—Length: approximately 1.5 cm on average. — diameter: approximately 2.0 mm on average. — texture: glabrous. — color of upper and lower surfaces: Yellow-Green Group 144A.

Inflorescence:

*Lastingness of individual inflorescence on the plant*.—Approximately 7-10 days on average.

*Fragrance*.—Strongly fragrant; fragrance sweet and pleasant.

*Inflorescence height*.—Approximately 20.0 cm on average.

*Inflorescence diameter*.—Approximately 12.0 cm on average.

*Flower arrangement and flowering habit*.—Single salverform flowers arranged in terminal panicles; freely flowering habit with usually about 250 flowers per inflorescence; flowers face upright to slightly outwardly.

*Flowering season*.—Plants of the new *Syringa* plant flower in early spring in Cochranville, Pennsylvania; flowers not persistent.

*Flower*.—Diameter: approximately 1.7 cm on average. — length (height): approximately 1.5 cm on average. — throat diameter: approximately 2.0 mm on average. — tube length: approximately 8.0 mm on average. — tube diameter, proximally: approximately 2.0 mm on average.

*Flower buds*.—Length: approximately 4.0 mm on average. — diameter: approximately 4.0 mm on average. — shape: ovate. — color: Purple Group N77C.

*Petals*.—Quantity and arrangement: single whorl of four petals; lower portion of petals fused forming a narrow tube. — lobe length: approximately 1.0 cm on average. — lobe width: approximately 9.0 mm on average. — lobe shape: ovate. — apex: obtuse to acute, curling inwards. — margin: entire. — texture, upper and lower surfaces: smooth, glabrous. — texture, throat and tube: smooth, glabrous. — color when opening and fully opened, upper and under surfaces: Purple Group 76A and fading to Purple Group 76B.

*Sepals*.—Quantity and arrangement: single whorl of four sepals; fused towards the base forming a campanulate-shaped calyx. — length: approximately 2.0 mm on average. — width: approximately 1.0 mm on average. — shape: narrowly deltoid. — apex: acute. — margin: entire. — texture, upper and lower surfaces: glabrous. — color, upper and lower surfaces: Purple Group N77C.

*Peduncles*.—Length: approximately 2.5 cm on average. — diameter: approximately 3.0 mm on average. — strength: strong. — aspect: approximately 45 degrees to 90 degrees from stem axis. — texture: smooth, glabrous. — color: Grey-Brown Group N200B.

*Pedicels*.—Length: approximately 5.0 mm on average. — diameter: approximately 1.0 mm on average. — strength: strong. — aspect: approximately 45 degrees from peduncle axis. — texture: smooth, glabrous. — color: Yellow-Green Group 144A.

*Reproductive organs*.—

*Androecium*.—Stamen quantity: 2 per flower. — stamen length: approximately 2.0 mm on average. — anther shape: oblong. — anther length: approximately 2.0 mm on average. — anther color: Yellow Group 5B. — pollen amount: moderate. — pollen color: Yellow Group 5C.

*Gynoecium*.—Pistil quantity: 1 per flower. — pistil length: approximately 3.0 mm on average. — stigma shape: conical. — stigma length: approximately 1.0 mm on average. — stigma color: Green-Yellow Group 1C. — style length: approximately 2.0 mm on average. — style color: Green-Yellow Group 1D. — ovary diameter: approximately 1.0 mm on average. — ovary color: Green Group 143C.

*Seed and fruit production*.—Neither seed nor fruit production has been observed.

Development:

*Vegetation*.—Moderately vigorous.

*Disease and pest resistance*.—Strongly resistant to Lilac Powdery Mildew (*Erysiphe syringae*), plants of the new *Syringa* variety have not been observed to be resistant to pests common to *Syringa* plants.

The new 'G13110' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Syringa* plant named 'G13110' characterized by the following combination of characteristics:

(a) forms light pink colored, strongly fragrant flowers, (b) exhibits dark green-colored foliage, and (c) displays a densely branched and compact growth habit;

substantially as herein shown and described.

* * * * *